United States Patent [19]
Glas et al.

[11] Patent Number: 5,599,937
[45] Date of Patent: Feb. 4, 1997

[54] HETEROAROMATIC QUINUCLIDINENES, THEIR USE AND PREPARATION

[75] Inventors: Gunilla Glas, Kista; Uli Hacksell, Uppsala; Gary Johansson, Uppsala; Björn Nilsson, Uppsala; Lisbeth Nilvebrant, Bromma; Gunnar Nordvall, Södertälje, all of Sweden

[73] Assignee: Pharmacia AB, Stockholm, Sweden

[21] Appl. No.: 325,407

[22] PCT Filed: May 11, 1993

[86] PCT No.: PCT/SE93/00415

§ 371 Date: Nov. 8, 1994

§ 102(e) Date: Nov. 8, 1994

[87] PCT Pub. No.: WO93/23395

PCT Pub. Date: Nov. 25, 1993

[30] Foreign Application Priority Data

May 11, 1992 [SE] Sweden .................................. 9201478

[51] Int. Cl.⁶ ..................... C07D 453/02; A61K 31/44
[52] U.S. Cl. ............................................. 546/133
[58] Field of Search ..................... 546/133, 134; 514/305

[56] References Cited

FOREIGN PATENT DOCUMENTS

| | | |
|---|---|---|
| 0261763 | 3/1988 | European Pat. Off. . |
| 0287356 | 10/1988 | European Pat. Off. . |
| 0301729 | 2/1989 | European Pat. Off. . |
| 0307141 | 3/1989 | European Pat. Off. . |
| 0307142 | 3/1989 | European Pat. Off. . |
| 0316718 | 5/1989 | European Pat. Off. . |
| 0328200 | 8/1989 | European Pat. Off. . |
| 0363085 | 4/1990 | European Pat. Off. . |
| 0427390 | 5/1991 | European Pat. Off. . |
| 0450345 | 10/1991 | European Pat. Off. . |

OTHER PUBLICATIONS

CA115:214996 (Barnaby, J. Liq. Chromatogr. (1991) 14(2), 287–95), 1991.
CA113:231362 (Orlek, EP 366304, May 2, 1990), 1990.
CA113:152390 (Baker, EP 337547, Oct. 18, 1989), 1990.
CA112:158157 (Saunders, J. Med. Chem (1990), 33(4) 1128–38), 1990.
CA112:138925 (Orlek, EP 322182, Jun. 28, 1989), 1990.
CA110:115165 (JP 63/039876 Feb. 20, 1988), 1989.
J. Med. Chem., vol. 33, 1990, John Saunders et al, pp. 1128–1138.

*Primary Examiner*—Shean C. Wu
*Attorney, Agent, or Firm*—Birch, Stewart, Kolasch & Birch, LLP

[57] ABSTRACT

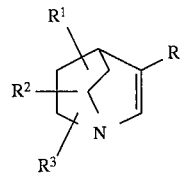

(I)

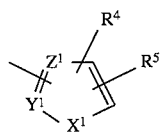

(II)

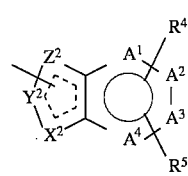

(III)

The invention relates to novel compounds of general formula (I), wherein R is a group of general formula (II) or (III), where $X^1$ represents oxygen or sulphur and $Y^1$ and $Z^1$ both represent carbon, or $X^1$ represents oxygen and one of $Y^1$ and $Z^1$ represents nitrogen and the other represents carbon, or $X^1$ represents sulphur, $Y^1$ represents nitrogen and $Z^1$ represents carbon; one of $X^2$, $Y^2$ and $Z^2$ represents oxygen or sulphur and the other two both represent carbon or one represents nitrogen and the other represents carbon, and the dotted line in formula (III) represents an optional additional carbon-carbon or carbon-nitrogen bond; $A^1$, $A^2$, $A^3$ and $A^4$ each represent carbon or, when one of $X^2$, $Y^2$ and $Z^2$ represents oxygen or sulphur and the other two both represent carbon, one or two of $A^1$, $A^2$, $A^3$ and $A^4$ may represent nitrogen and the others carbon; and $R^1$ to $R^5$ are as defined in the description. The compounds of formula (I) can be used for treating diseases related to muscarinic receptor function.

11 Claims, No Drawings

HETEROAROMATIC QUINUCLIDINENES, THEIR USE AND PREPARATION

This application is a 371 of PCT/SE93/00415 filed May 11, 1993.

FIELD OF THE INVENTION

The present invention relates to novel chemical compounds having activity at central and peripheral nervous systems, pharmaceutical compositions containing them, the use of the compounds for preparing medicaments, and processes for their preparation.

BACKGROUND OF THE INVENTION AND PRIOR ART

Acetylcholine is one of the most important neurotransmitters in the central and peripheral nervous systems. Receptors mediating the actions of acetylcholine are subdivided into nicotine-like and muscarine-like, based on the action of particular agonists and antagonists.

The cholinergic receptors in the central nervous system of mammals are mainly muscarinic. Cholinergic deficiencies in the central nervous system have been implicated in several neurological and mental illnesses, such as Alzheimer's disease and senile dementia of the Alzheimer type. Muscarinic agonists capable of increasing the cholinergic transmission in the brain, particularily in the cortex, may therefore be of therapeutic value in the treatment of Alzheimer's disease and other diseases related to impairment of the cholinergic nervous system.

Muscarinic receptors in the peripheral nervous system mediate the actions of acetylcholine at parasympathetic postganglionic neuroeffector junctions. Evidence also indicate that muscarinic receptors can modulate transmission in autonomic ganglia. Muscarinic presynaptic receptors regulating transmitter release are present in the central as well as peripheral nervous system.

Stimulation of postsynaptic peripheral receptors generate numerous physiological responses, including smooth muscle contraction, secretion by various glands, bronchoconstriction, relaxation of vascular smooth muscles, decrease in the cardiac rate and force of contraction.

Among the various compounds which are described in the prior art as having activity on muscarinic receptors are, for instance, derivatives based upon azabicyclic alkanes, particularly azabicyclo[2.2.2]octane (quinuclidine) and azabicyclo[2.2.1]heptane derivatives. Thus, for example, EP-A-301 729 discloses oxadiazolyl-substituted quinuclidine and quinuclidinene compounds which are potent muscarinic agonists.

EP-A-307 142 discloses oxathiazolyl-substituted quinuclidine and quinuclidinene compounds having potent muscarinic agonist activity.

EP-A-307 141 discloses oxazolyl- and thiazolyl-substituted quinuclidines and quinuclidinenes which stimulate muscarinic acetylcholine receptors.

EP-A-287 356 discloses oxazolyl-substituted azabicyclo [3.2.1]octanes which enhance acetylcholin function via an action at muscarinic receptors.

EP-A-363 085 discloses azabicyclo[2.2.2]octanes and -[2.2.1]heptanes substituted by oxazolyl, oxadiazolyl, thiadiazolyl, thiazolyl, furyl, triazolyl or tetrazolyl groups, which compounds enhance acetylcholine function via muscarinic receptors.

EP-A-316 718 discloses oxadiazolyl- and isoxazolyl-8-azabicyclo[3.2.1]oct-2-enes having muscarinic cholinergic receptor antagonistic activity.

EP-A-328 200 discloses methylindolyl-oxadiazolyl-quinuclidines having 5-HT$_3$ receptor activity.

EP-A-450 345 discloses 3-(3-indolyl)-quinuclidines and quinuclidinenes which antagonize the activity of serotonin on 5-HT$_3$ receptors.

EP-A-261 763 discloses oxadiazolyl- and thia(dia)zolyl-quinuclidines which enhance acetylcholine function via an action at muscarinic receptors.

EP-A-427 390 disclose pyrazol-, triazol- and tetrazol-quinuclidines and -quinuclidinenes which enhance acetylcholine function via muscarinic receptors.

J. Med. Chem. 33 (1991) 1128–1138 discloses a series of heterocyclic substituted quinuclidines spanning the activity range from efficacious muscarinic agonists, through partial agonists, to muscarinic antagonists. Among the substituent heterocycles are oxazolyl, furyl, methylfuryl and methyloxazolyl. The specific compounds 3-(5-methyl-2-furyl)quinuclidinene, 3-(4-methyl-2-furyl)quinuclidinene and 3-(2-furyl)quinuclidinene are only disclosed as non-isolated intermediates in the preparation of the corresponding quinuclidines.

SUMMARY OF THE INVENTION

The object of the present invention is to provide a class of novel substituted quinuclidinene derivatives which block or stimulate muscarinic acetylcholine receptors, centrally or peripherally, and therefore are of potential use for the treatment of diseases where cholinergic receptors are involved.

Accordingly, the present invention provides novel compounds of the general Formula I:

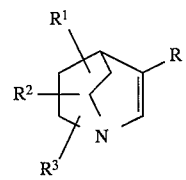

wherein

R is a group of the general Formula II or III:

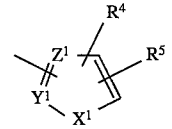

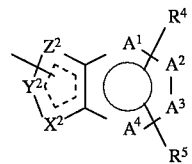

where $X^1$ represents oxygen or sulphur and $Y^1$ and $Z^1$ both represent carbon, or $X^1$ represents oxygen and one of $Y^1$ and $Z^1$ represents nitrogen and the other represents carbon, or $X^1$ represents sulphur, $Y^1$ represents nitrogen and $Z^1$ represents carbon;

one of $X^2$, $Y^2$ and $Z^2$ represents oxygen or sulphur and the other two both represent carbon or one represents nitrogen and the other represents carbon, and the dotted line in Formula III represents an optional additional carbon-carbon or carbon-nitrogen bond;

$A^1$, $A^2$, $A^3$ and $A^4$ each represent carbon or, when one of $X^2$, $Y^2$ and $Z^2$ represents oxygen or sulphur and the other two both represent carbon, one or two of $A^1$, $A^2$, $A^3$ and $A^4$ may represent nitrogen and the others carbon;

$R^1$, $R^2$ and $R^3$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $C_{1-10}$alkoxy, $C_{2-10}$alkenyloxy, $C_{2-10}$alkynyloxy, $C_{3-10}$cycloalkyloxy, $C_{5-10}$cycloalkenyloxy, $C_{4-10}$cycloalkylalkoxy, $C_{6-10}$cycloalkylalkenyloxy, hydroxy, hydroxy-$C_{1-10}$alkyl, or $(CH_2)_n Ar$, where Ar is optionally substituted aryl or heteroaryl, the latter containing 1 to 3 heteroatoms selected from oxygen, sulphur and nitrogen, and n is an integer 0 to 10; and $R^4$ and $R^5$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, halogen or $(CH_m)_n B$, wherein $(CH_m)_n$, in which n is as defined above and m independently is an integer 0 to 2, represents a bond or a straight or branched, saturated or unsaturated hydrocarbon chain and B represents Ar (as defined above), $COR^6$, $COOR^6$, $CON(R^6)_2$, $N(R^6)_2$, $OR^6$, $CN$, $NO_2$, $C=NOR^6$, $OCOR^6$, $N(R^6)COR^6$, $C(R^6)_2 OR^6$, $OCOC(OH)(R^6)_2$ or trifluoromethyl, where $R^6$ independently represents hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $(CH_2)_n Ar$ or a bi- or tricyclic ring system comprising 0 to 3 ring hetero atoms, wherein Ar and n are as defined above; or $R^4$ and $R^5$ are interconnected to complete a saturated or unsaturated ring which may contain 1 or 2 hetero atoms;

with the proviso that when R represents a group of Formula II and $R^1$, $R^2$ and $R^3$ each are hydrogen, R is other than 2-furyl, 4-methyl-2-furyl and 5-methyl-2-furyl; and physiologically acceptable salts thereof.

The invention also provides a pharmaceutical composition comprising a compound of the general Formula IA:

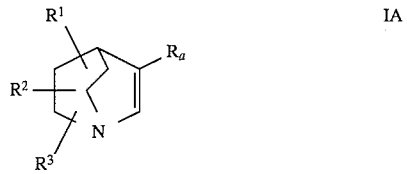

wherein $R^1$, $R^2$ and $R^3$ are as defined above, and $R_a$ is as defined above for R and additionally may represent 2-furyl, 4-methyl-2-furyl and 5-methyl-2-furyl also when $R^1$, $R^2$ and $R^3$ are hydrogen.

The invention additionally provides the use of the compounds of Formula IA above for the manufacture of a medicament for the prevention or treatment of a disease or disorder related to muscarinic receptor function.

The invention further provides a therapeutical method which comprises administering a compound of Formula IA to a subject in need thereof.

Processes for the production of the compounds of Formula I as well as intermediate products used therein are also included in the invention as will be described further below.

DETAILED DESCRIPTION OF THE INVENTION

In the compounds of Formula I and IA above, $C_{1-10}$alkyl and $C_{1-10}$alkoxy are straight or branched and are preferably $C_{1-6}$alkyl and $C_{1-6}$alkoxy, respectively, and more preferably $C_{1-4}$alkyl and $C_{1-4}$alkoxy, respectively. Illustrative examples include methyl, ethyl, n-propyl, iso-propyl, n-butyl, tert-butyl, n-pentyl, n-hexyl and the corresponding alkoxy groups.

$C_{2-10}$alkenyl and $C_{2-10}$alkenyloxy are straight or branched and are preferably $C_{2-6}$alkenyl and $C_{2-10}$alkenyloxy, respectively, and more preferably $C_{2-4}$alkenyl and $C_{2-4}$alkenyloxy, respectively. Illustrative examples include ethenyl, 2-propenyl, 3-butenyl, 1-methyl-2-propenyl, 2-pentenyl, 2-ethyl-3-butenyl and 4-hexenyl, and the corresponding alkenyloxy groups.

$C_{2-10}$alkynyl and $C_{2-10}$alkynyloxy are straight or branched and are preferably $C_{2-6}$alkynyl and $C_{3-6}$alkynyloxy, respectively, and more preferably $C_{2-4}$alkynyl and $C_{3-4}$alkynyloxy, respectively. Illustrative examples include ethynyl, 2-propynyl, 1-methyl-2-propynyl, 3-butynyl, 1-ethyl-2-propynyl, 1-methyl-3-butynyl, 4-pentynyl, and 5-hexynyl, and the corresponding alkynyloxy groups.

$C_{3-10}$cycloalkyl and $C_{3-10}$cycloalkyloxy are preferably $C_{3-8}$cycloalkyl and $C_{3-8}$cycloalkyloxy, respectively, such as cyclopropyl, cyclobutyl, cyclopentyl, cyclohexyl, and the corresponding cycloalkyloxy groups. Also alkyl-substituted carbocyclic rings are included, for example, methyl-, dimethyl- and ethylcyclohexyl.

$C_{5-10}$cycloalkenyl and $C_{5-10}$cycloalkenyloxy are preferably $C_{3-8}$cycloalkenyl and $C_{3-8}$cycloalkenyloxy, respectively, such as cyclopentenyl, cyclohexenyl, methyl-, dimethyl- and ethylcyclohexenyl, and the corresponding cycloalkenyloxy groups.

Exemplary of $C_{4-10}$cycloalkylalkyl and $C_{4-10}$cycloalkylalkoxy are cyclopentylmethyl, cyclopentylethyl, cyclohexylmethyl, cyclohexylethyl, and the corresponding cycloalkylalkoxy groups.

Exemplary of $C_{6-10}$cycloalkylalkenyl and $C_{6-10}$cycloalkylalkenyloxy, respectively, are cyclopentylethenyl, cyclopentylpropenyl, cyclohexylethenyl and cyclohexylpropenyl, and the corresponding cycloalkylalkenyloxy groups.

The term halogen includes fluorine, chlorine, bromine and iodine.

Aryl is preferably phenyl or naphthyl, more preferably phenyl.

Heteroaryl may, for example, be monocyclic, such as tiophene, furan, pyrrole, imidazole, pyrazole, thiazole, isothiazole, oxazole, isoxazole, triazole, pyridine, pyrazine, pyrimidine, pyridazine, or bicyclic, such as benzofuran, isobenzofuran, benzothiazole, benzothiophene, indole, isoindole, oxadiazole, benzoxazole.

Phenyl and heteroaryl may be substituted by one or more substituents selected from $C_{1-6}$alkyl, $C_{1-6}$alkoxy, halogen, and the groups defined for B above except Ar.

$R^1$, $R^2$ and $R^3$ may each independently be bound in any one of positions 2, 4, 5, 6, 7 and 8, and, except when representing hydrogen, also in position 1 of the quinuclidinene ring. Preferably, $R^1$, $R^2$ and $R^3$ are each hydrogen (i.e. the quinuclidinene ring is only substituted in position 3).

Exemplary of groups of Formulae II and III are:

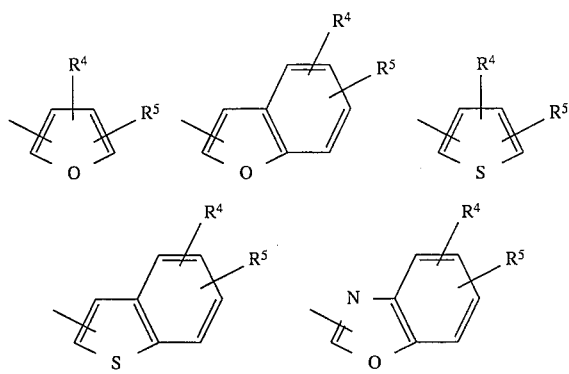

The groups of Formulae II and III may be connected to the 3-position of the quiniclidinene ring via any carbon atom of the five-membered heterocyclic ring.

$R^4$ and $R^5$ may be bound to any carbon atom of the heterocyclic ring or ring system, except the position of connection to the quinuclidinene ring.

Preferably, $R^4$ and $R^5$ independently are hydrogen, $C_{1-10}$alkyl, optionally substituted aryl or heteroaryl or the group $(CH_m)_nB$ as defined above. In a preferred group of compounds, one of $R^4$ and $R^5$ represents hydrogen and the other $C_{1-6}$alkyl or optionally substituted phenyl.

n is preferably 0–6, more preferably 0–3.

B is preferably $N(R^6)_2$, $OR^6$, C=NOH, $OCOR^6$, $N(R^6)COR^6$ or $C(R^6)_2OR^6$.

The straight or branched, saturated or unsaturated hydrocarbon chain $(CH_m)_n$ is preferably unsaturated, containing one or more, such as one or two, double and/or triple bonds. Preferably, the hydrocarbon chain has up to six carbon atoms. Exemplary of the group $(CH_m)_n$ are methylene, allylene, ethylene, vinylene, acetylene, etc.

When $R^6$ represents a bi- or tricyclic ring system, at least one of the rings may be heterocyclic. For example, a tricyclic ring system may comprise a phenyl ring flanked by two heterocyclic rings, a heterocyclic ring fused to naphthyl, or a heterocyclic ring flanked by two phenyl rings. Preferably, the ring system is bicyclic, for example consisting of naphthyl or phenyl fused to a heterocyclic ring, or of two fused heterocyclic rings. Exemplary heterocycles are those mentioned above for the definition of heteroaryl.

Preferably, $R^6$ is independently hydrogen, $C_{1-6}$alkyl, $C_{2-6}$alkenyl, $C_{2-6}$alkynyl, $C_{3-8}$cycloalkyl, $C_{3-8}$cycloalkenyl or optionally substituted phenyl or furyl, more preferably $C_{2-6}$alkynyl or optionally substituted phenyl.

When $R^4$ and $R^5$ are interconnected to form, together with part of the heteroaryl group to which they are bound, a saturated or unsaturated, optionally heterocyclic ring, such a ring may be a $C_{3-10}$cycloalkyl, $C_{3-10}$cycloalkenyl or an aryl or heteroaryl ring, such as a cyclohexane, benzene, piperidine, pyridazine or pyridine ring fused to the heteroaryl group of Formula II or III above.

In a preferred subgroup of the compounds of Formula I, $R^1$, $R^2$ and $R^3$ are each hydrogen and R is an optionally substituted furyl, thienyl or benzofuryl ring.

Due to the basic nitrogen of the quinuclidinenyl ring, the compounds of Formula I may form addition salts with pharmaceutically and physiologically acceptable organic or inorganic acids, and the invention comprises the free bases as well as the salts thereof. Examples of addition salt forming acids are oxalic acid, fumaric acid, malic acid, maleic acid, succinic acid, methane sulfonic acid, acetic acid, benzoic acid, hydrochloric acid, sulphuric acid, phosphoric acid, and the like. When one of $R^1$, $R^2$ or $R^3$ (other than hydrogen) is bound to the nitrogen atom of the quinuclidinene ring, the compounds of Formula I form quaternary amine salts, which salts are likewise encompassed by the invention.

When the novel compounds can be in the form of optical isomers, the invention comprises the racemic mixture as well as the individual enantiomers as such.

Specific compounds within the scope of the present invention include, but are not limited to the following:
3-(2-furyl)quinuclidin-2-ene
3-(3-furyl)quinuclidin-2-ene
3-(5-ethyl-2-furyl)quinuclidin-2-ene
3-(3-bromo-2-furyl)quinuclidin-2-ene
3-(3-thienyl)quinuclidin-2-ene
3-(2-thienyl)quinuclidin-2-ene
3-(5-methyl-2-furyl)quinuclidin-2-ene
3-(3-phenyl-2-furyl)quinuclidin-2-ene
3-(5-methyl-2-thienyl)quinuclidin-2-ene
3-(5-phenyl-2-furyl)quinuclidin-2-ene
3-(3-methyl-2-furyl)quinuclidin-2-ene
3-(5-methoxycarbonyl-2-furyl)-quinuclidin-2-ene
3-(2-benzofuryl)quinuclidin-2-ene
3-(5-bromo-2-benzofuryl)-quinuclidin-2-ene
3-(2-benzothienyl)quinuclidin-2-ene
3-(3-benzothienyl)quinuclidin-2-ene
3-(benzothiazol-2-yl)quinuclidin-2-ene
3-[5-(N-phenylcarbamoyl)-2-furyl]-quinuclidin-2-ene
3-(benzoxazol-2-yl)quinuclidin-2-ene
3-(5-butyl-2-furyl)quinuclidin-2-ene
3-(5-acetyl-2-furyl)quinuclidin-2-ene
3-(4-acetyl-2-furyl)quinuclidin-2-ene
3-(4-phenyl-2-furyl)quinuclidin-2-ene
3-(5-acetyl-2-thienyl)quinuclidin-2-ene
3-(5-formyl-2-thienyl)quinuclidin-2-ene
3-(5-formyl-7-methoxy-2-benzofuryl)quinuclidin-2-ene
3-(5-hydroxymethyl-7-methoxy-2-benzofuryl)quinuclidin-2-ene
3-(7-hydroxymethyl-5-iodo-2-benzofuryl)quinuclidin-2-ene
3-(7-iodo-5-nitro-2-benzofuryl)quinuclidin-2-ene
3-(5-cyano-7-iodo-2-benzofuryl)quinuclidin-2-ene.

The compounds of the present invention having antimuscarinic activity are useful for the treatment of extrapyramidal motor disorders, Parkinsonism, disorders affecting the parasympathetic nervous system, spastic states affecting the gastrointestinal channel, gall bladder and kidneys, ulcus ventriculi and duodeni, hypersecretion, bradycardia, hyperhidrosis, disorders affecting the pulmonary system, and for treatment of disorders of the urinary bladder such as motor urge incontinence.

Compounds of the present invention being agonists, and/or partial agonists having specific presynaptic antimuscarinic activity and displaying central nervous system activity, may potentially be used for the treatment of memory dysfunctions, senile dementia, Alzheimer's disease, schizophrenia, Huntington's chorea, tardive dyskinesia, and as analgesics for the treatment of pain, and as sleep aids.

Compounds of the present invention being agonists may potentially be used for treatment of disorders affecting the parasympathetic nervous system such as urinary retention, atony of the gastrointestinal channel, kidneys, and gall bladder, and glaucoma.

The compounds of the general Formula IA above, in the form of free bases or salts of acceptable organic or inorganic acids, can be brought into suitable galenic forms, such as formulations for oral, transdermal, or intranasal use, and for injection, or the like, in accordance with conventional pharmaceutical procedures. Such formulations comprise the active compound in association with pharmaceutically acceptable carriers. The carriers may be any inert material, organic or inorganic, suitable for enteral, percutaneous or parenteral administration, such as water, gelatin, gum arabicum, lactose, cellulose, starch, sodium starch glycolate, cyclodextrins, calcium hydrogen phosphate, magnesium stearate, talcum, colloidal silicon dioxide, stabilizers, wetting agents, emulsifiers, flavouring agents, buffers, and the like.

The pharmaceutical formulations according to the invention comprise solid as well as liquid dosage forms, such as tablets, capsules, powders, syrups, elixirs, depots, sterile solutions, suspensions or emulsions, and the like for oral and parenteral administration.

The dosage of the compound of Formula IA to be administered will, of course, depend on the potency of the selected specific compound, the mode of administration, the age and weight of the patient, the severity of the condition to be treated, and the like. The daily dosage may, for example, be from about 0.001 mg to about 25 mg per kilo of body weight, administered in one or more doses. The compositions of the invention are preferably formulated in a unit dosage form, containing, for example, about 0.05 to about 500 mg of the active ingredient.

The compounds according to the invention can be prepared according to per se conventional methods using starting materials which are either commercially available, or can be prepared by methods known from the literature, or as described herein. More particularly, the present invention provides processes for the preparation of the novel compounds of Formula I, which processes comprise:

(a) dehydrating a compound of the general Formula IV:

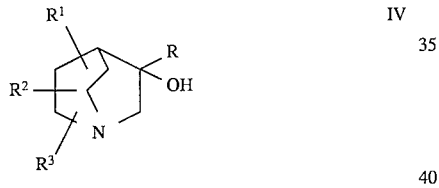

wherein R, $R^1$, $R^2$ and $R^3$ are as defined in claim 1; or (b) for the preparation of a compound of Formula I wherein $R^4$ and $R^5$ are as defined in claim 1 except that $R^5$ is other than hydrogen, reacting, in the presence of a metal catalyst, a compound of the general Formula V or VI:

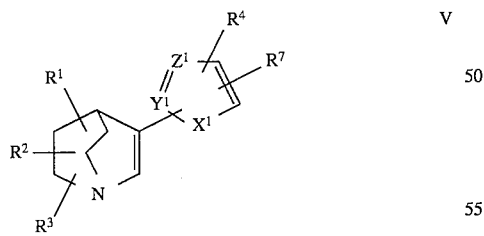

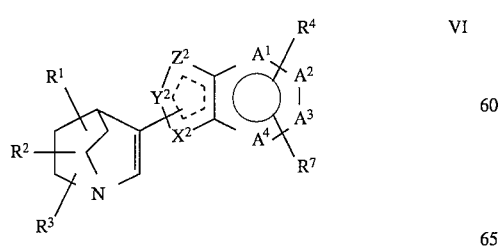

with a compound $R^8$-D, wherein $X^1$, $Y^1$, $Z^1$, $X^2$, $Y^2$, $Z^2$ and $R^4$ are as defined in claim 1, D is $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $(CH_2)_n$Ar or $(CH_m)_n$B, where Ar, n, m and B are as defined above, and one of $R^7$ and $R^8$ represents halogen, triflate or mesylate, preferably halogen or triflate, and the other represents a group selected from $Sn(Alk)_3$, $Si(Alk)_3$, ZnHal, $Al(R^9)_2$, $TlX_2$, HgX and $B(OR^9)_2$, where Alk is alkyl of from 1 to 10 carbon atoms, Hal is halogen, X is halogen, acetate or trifluoroacetate, and $R^9$ is hydrogen or Alk; or $R^7$ represents halogen, triflate or mesylate, preferably halogen or triflate, and $R^8$-D is $C_{2-10}$alk-1-yn;

(c) for the preparation of a compound of Formula I wherein $R^4$ and $R^5$ are as defined in claim 1 except that $R^5$ is other than hydrogen, generating the carbanion of a compound of the general Formula VII or VIII:

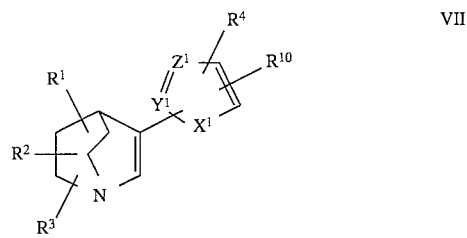

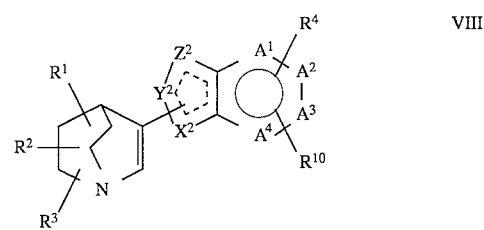

wherein $X^1$, $Y^1$, $Z^1$, $X^2$, $Y^2$, $Z^2$ and $R^4$ are as defined in claim 1, and $R^{10}$ represents hydrogen or halogen, and reacting the carbanion formed with an electrophilic reagent capable of forming the desired substituent $R^5$;

(d) reacting, in the presence of a metal catalyst, a compound of the general Formula IX:

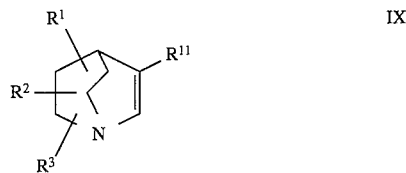

with a compound R—E, wherein R, $R^1$, $R^2$ and $R^3$ are as defined in claim 1, and one of $R^{11}$ and E represents halogen, triflate or mesylate, preferably halogen or triflate, and the other represents a group selected from $Sn(Alk)_3$, $Si(Alk)_3$, ZnHal, $Al(R^9)_2$, $TlX_2$, HgX, and $B(OR^9)_2$, where Alk is alkyl of from 1 to 10 carbon atoms, Hal is halogen, X is halogen, acetate or trifluoroacetate and $R^9$ is hydrogen or Alk;

(e) for the preparation of compounds of Formula I, wherein R is a group of Formula III, in which $A^1$ to $A^4$ each are carbon or one or two of $A^1$ to $A^4$ are nitrogen and the others are carbon, $X^2$ is oxygen or sulphur and $Y^2$ and $Z^2$ both are carbon, reacting a compound or intermediate of the general Formula X:

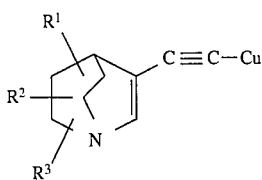

wherein $R^1$, $R^2$ and $R^3$ are as defined in claim 1, with a compound of the general Formula XI:

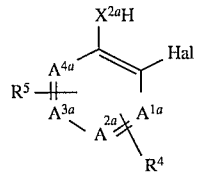

wherein $R^4$ and $R^5$ are as defined in claim 1, Hal represents halogen, $X^{2a}$ represents oxygen or sulphur, and $A^{1a}$ to $A^{4a}$ each represent carbon or one or two of of $A^{1a}$ to $A^{4a}$ represent nitrogen and the others represent carbon;

(f) for the preparation of compounds of Formula I, wherein R is a group formula III, in which $A^1$ to $A^4$ each are carbon or one or two of $A^1$ to $A^4$ are nitrogen and the others are carbon, $X^2$ is oxygen or sulphur and $Y^2$ and $Z^2$ both are carbon, reacting a compound or intermediate of the general Formula XII:

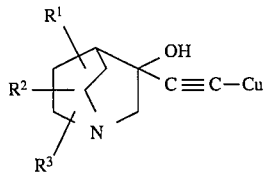

wherein $R^1$, $R^2$ and $R^3$ are as defined in claim 1, with a compound of Formula XI as defined in process e) above, and then dehydrating the product formed;

(g) in a compound of Formula I, converting a group $R^4$ or $R^5$ into another group $R^4$ or $R^5$;

and, if desired, forming a physiologically acceptable salt with an organic or inorganic acid.

The dehydration in processes a) and f) may be performed by acid-catalyzed dehydration, usually at elevated temperature, e.g. up to 250° C. Suitable acids are, e.g., formic and methanesulfonic acids. Alternatively, the hydroxy group may be removed by halogen substitution and subsequent elimination thereof. Chlorination may, for example, be effected by treatment with phosphorus oxychloride in the presence of triethylamine, or with thionyl chloride followed by e.g. diazabicyclononane (DBN) treatment.

The starting compounds of Formula IV in process a), except the compounds wherein $R^1$, $R^2$, and $R^3$ each are hydrogen and R is 2-furyl, 4-methyl-2-furyl or 5-methyl-2-furyl, are novel and also form part of the present invention.

The compounds of Formula IV may be prepared by reacting 3-quinuclidinone with the anion of the heterocycle corresponding to the group R in Formula IV in a nucleophilic carbonyl addition reaction. Such heterocyclic anion may be prepared by treating the heterocycle or a halogen-substituted heterocycle with n-butyl lithium or lithium diisopropylamide in a solvent, such as tetrahydrofuran or diethylether, at reduced temperature, e.g. in the range −100° C. to 0° C.

In process b), when $R^7$ is halogen, such as bromine, triflate or mesylate, a desired alkyl, alkenyl, alkynyl, aryl or heteroaryl substituent may be introduced by metal-catalyzed coupling (e.g. Pd, Ni) of the compound of Formula V or VI with (i) e.g. the corresponding tetralkyl tin, alkenyltrialkyl tin, alkynyltrialkyl tin, aryltrialkyl tin, heteroaryltrialkyl tin or alkyn reagent, or (ii) e.g. the corresponding aryl or heteroaryl boronic acid, or aryl or heteroaryldialkyl boronic acid ester.

When $R^7$ is $Sn(Alk)_3$, $Si(Alk)_3$, ZnHal, $Al(R^9)_2$, $TlX_2$, or HgX, a desired aryl or heteroaryl substituent may be introduced by metal-catalyzed coupling (e.g. Pd, Ni) of the compound of Formula V or VI with the corresponding aryl halogen, triflate or mesylate, or heteroaryl halogen, triflate or mesylate compound.

A trialkylstannyl compound V or VI ($R^7$ is $Sn(Alk)_3$) may, for example, be prepared by lithiation of the corresponding $R^7$-unsubstituted, and when necessary halogenated, compound in a solvent, such as tetrahydrofuran or diethyl ether, at reduced temperature and quenching of the anion with trialkyltin chloride.

When $R^7$ in Formula V or VI is $B(OH)_2$ or $B(OAlk)_2$, a desired aryl or heteroaryl substituent may be introduced by metal-catalyzed coupling (e.g. Pd, Ni) of the compound of Formula V or VI with the corresponding aryl halogen, triflate or mesylate, or heteroaryl halogen, triflate or mesylate compound.

A dialkylboronic ester compound V or VI ($R^7$ is $B(OAlk)_2$) may, for example, be prepared by lithiation of the corresponding $R^7$-unsubstituted compound with n-butyl lithium in a solvent, such as tetrahydrofuran or diethyl ether, at reduced temperature, and quenching the anion with trialkyl borate.

In process c), the carbanion of the compound of Formula VII or VIII may be generated by O-lithiation, halogen-metal exchange or generation of a Grignard reagent. The electrophilic reagent used to quench the carbanion to produce the final product is selected depending on the desired substitution, and may e.g. be an aldehyde or a ketone (forming a hydroxyalkyl, -aryl or -heteroaryl substituent), a nitrile or acid chloride (forming a keto substituent), an alkyl halide (forming an alkyl substituent), or molecular halogen (forming a halogen substituent).

The starting Compounds of Formula IX in process d) in which $R^{11}$ is $Sn(Alk)_3$, $Si(Alk)_3$, ZnHal, $Al(R^9)_2$, $TlX_2$, HgX or $B(OR^9)_2$, may be prepared by reacting 3-quinuclidinone with 2,4,6-triisopropylbenzenesulfonyl hydrazide to give 3-(2,4,6-triisopropylbenzenesulfonyl hydrazone)quinuclidine. The latter compound is then treated with two equivalents of n-butyl lithium at reduced temperature in a solvent, such as TMEDA/hexane or tetrahydrofuran, and subsequently quenched with the appropriate reagent, such as with trialkyltin chloride to give 3-trialkylstannyl-quinuclidin-2-ene, or with trialkyl borate to give the 3-alkylboronic acid ester of the quinuclidine-2-ene or the 3-boronic acid of the quinuclidin-2-ene.

The starting compounds of Formula IX in process d) in which $R^{11}$ is halogen, may be prepared by reacting the 3-quinuclidinone with 2,4,6-triisopropylbenzenesulfonyl hydrazide to give 3-(2,4,6-triisopropylbenzenesulfonyl-hydrazone)-quinuclidine. This compound is then treated with 2 equivalents of n-butyllithium at reduced temperature in a solvent, such as TMEDA/hexane or THF, and subsequently quenched with an electrophilic halogen reagent (such as $Br_2$, $I_2$ or N-bromosuccinimide (NBS)) to give the 3-halogenoquinuclidin-2-ene.

Processes e) and f) may be performed at elevated temperature in a solvent, such as pyridine. The starting compounds of Formula XI may be prepared as described by Grob et al, Helv. Chim. Acta, 1963, pages 2658–2666.

The invention will now be further illustrated by the following non-limiting examples.

GENERAL

Routine $^1$H and $^{13}$C NMR spectra were recorded at 90 and 22.5 MHz, respectively, on a JEOL FX 90Q spectrometer and were referenced to internal tetramethylsilane. All NMR spectra were in accordance with the assigned structures.

Melting points (uncorrected) were determined in open glass capillaries on a Thomas-Hoover apparatus.

Capillary GC was performed on a Carlo Erba 6000, by use of an SE 52 column (25 m) or DB5 column (25 m), equipped with a flame ionization detector (FID-40) and a Milton Roy CI-10B integrator. The elemental analyses, (C, H and N), which were within ±0.4% of the theoretical values, were performed by Mikro Kemi AB, Uppsala, Sweden.

EXAMPLE 1

3-(2-Thienyl)quinuclidin-3-ol, 0.5 Fumarate

A solution of n-butyllithium in hexane (17.6 mL, 1.35M, 23.7 mmol) was added dropwise to a stirred solution of thiophene (2.30 mL, 28.7 mmol) in dry ether (30 mL) at 0° C. A solution of 3-quinuclidinone (2.71 g, 21.6 mmol) in dry ether (30 mL) was added dropwise after standing for 2 hours and the mixture was allowed to warm to room temperature over 10 hours. The mixture was quenched with saturated ammonium chloride (10 mL, added dropwise), poured into 2M hydrochloric acid and washed with ether. The aqueous layer was basified with 5M sodium hydroxide; the product was extracted with ether, dried over potassium carbonate and concentrated in vacuo. Column chromatography on alumina with gradient elution [CHCl$_3$→CHCl$_3$/MeOH (95:5)] gave 4.03 g (89%) of the product, which was converted to the fumarate and recrystallized from Et$_2$O/MeOH/acetone: mp 208°–210° C.; Rf 0.25 in CHCl$_3$/MeOH (95:5) on alumina.

$C_{11}H_{15}NOS.0.5C_4H_4O_4$ requires: C, 58.4; H, 6.4; N, 5.2. Found: C, 58.2; H, 6.3; N, 5.1.

EXAMPLE 2

3-(2-Furyl)quinuclidin-3-ol, Fumarate

By essentially following the procedure in Example 1, substituting furan for thiophene, the title compound was prepared with a yield of 73%; mp 176.5°–177.5° C.

$C_{11}H_{15}NO_2.C_4H_4O_4$ requires: C, 58.2; H, 6.2; N, 4.5. Found: C, 58.3; H, 6.2; N, 4.5.

EXAMPLE 3

3-(3-Furyl)quinuclidin-3-ol, 0.5 Fumarate

A solution of n-butyllithium in hexane (14.2 mL, 1.5M, 21.3 mmol) was added dropwise to a solution of 3-bromofuran (2.2 mL, 23.9 mmol) in dry ether (40 mL) at −75° C. over 10 min. After 5 min., a solution of 3-quinuclidinone (2.66 g, 21.2 mmol) in dry ether (20 mL) was added, and the mixture was stirred at −75° C. for 4 hours. A solution of saturated aqueous ammonium chloride (1.5 mL) was added dropwise at −70° C., and the mixture was poured into 2.5M aqueous HCl and washed with ether. The aqueous layer was basified with 5M aqueous NaOH; the product was extracted with ether, dried (K$_2$CO$_3$), filtered, and concentrated in vacuo. Column chromatography on alumina, gradient eluted with CHCl$_3$→CHCl$_3$/MeOH (95:5), yielded 2.01 g (49%) of pure 3-(3-furyl)quinuclidin-3-ol, which was converted into the fumarate and recrystallized from acetone/MeOH; mp 207°–209° C.; Rf 0.21 in CHCl$_3$/MeOH on alumina. $C_{11}H_{15}NO_2.0.5C_4H_4O_4$ requires: C, 62.1; H, 6.8; N, 5.5. Found: C, 61.9; H, 6.9; N, 5.6.

EXAMPLE 4

3-(5-Methyl-2-furyl)quinuclidin-3-ol, 0.5 Fumarate

By essentially following the procedure in Example 1, substituting 2-methylfuran for thiophene, the title compound was prepared with a yield of 82%; mp 177.5°–178.5° C. $C_{12}H_{17}NO_2.0.5C_4H_4O_4$ requires: C, 63.4; H, 7.2; N, 5.3. Found: C, 63.3; H, 7.2; N, 5.2.

EXAMPLE 5

3-(3-Thienyl)quinuclidin-3-ol, 0.5 Fumarate

By essentially following the procedure in Example 3, substituting 3-bromothiophene for 3-bromofuran, the title compound was prepared with a yield of 50%; mp 219°–220° C. $C_{11}H_{15}NOS.0.5C_4H_4O_4$ requires: C, 58.4; H, 6.4; N, 5.2. Found: C, 58.2; H, 6.4; N, 5.2.

EXAMPLE 6

3-(5-Methylthienyl)quinuclidin-3-ol, 0.5 Fumarate 0.25 H$_2$O

By essentially following the procedure in Example 1, substituting 2-methylthiophene for thiophene, the title compound was prepared with a yield of 81%; mp 206°–206.5° C. $C_{12}H_{17}NOS.0.5C_4H_4O_4$ requires: C, 58.8; H, 6.9; N, 4.9. Found: C, 59.1; H, 6.8; N, 4.9.

EXAMPLE 7

3-(3-Bromo-2-furyl)quinuclidin-3-ol, 0.5 Oxalate 0.5 H$_2$O

By essentially following the procedure in Example 1, substituting 3-bromofuran for thiophene and lithium-diisopropyl amide for n-buthyllithium, the title compound was prepared with a yield of 82%; mp 225°–226° C. $C_{11}H_{14}BrNO.0.5(COOH)_2$ requires: C, 44.3; H, 4.9; N, 4.3. Found: C, 44.3; H, 4.6; N, 4.2.

EXAMPLE 8

3-(5-Ethyl-2-furyl)quinuclidin-3-ol, 0.5 Fumarate

By essentially following the procedure in Example 1, substituting 2-ethylfuran for thiophene, the title compound was prepared with a yield of 82%; mp 225°–226° C. $C_{13}H_{19}NO_2.0.5C_4H_4O_4$ requires: C, 64.5; H, 7.6; N, 5.0. Found: C, 64.6; H, 7.6; N, 4.8.

EXAMPLE 9

3-(2-Benzofuryl)quinuclidin-3-ol, 0.5 Fumarate

By essentially following the procedure in Example 1, substituting benzofuran for thiophene, the title compound was prepared with a yield of 79%; mp 203°–204° C. $C_{15}H_{17}NO_2.0.5C_4H_4O_4$ requires: C, 67.7; H, 6.3; N, 4.6. Found: C, 67.5; H, 6.3; N, 4.6.

EXAMPLE 10

3-(2-Benzothienyl)quinuclidin-3-ol, Hydrochloride

By following the procedure in Example 1, substituting benzothiophene for thiophene, the title compound was prepared with a yield of 66%; mp 219°–220° C. $C_{15}H_{17}NOS \cdot HCl$ requires: C, 60.9; H, 6.1; N, 4.7. Found: C, 61.0; H, 6.0; N, 4.7.

EXAMPLE 11

3-(3-Benzothienyl)quinuclidin-3-ol, Hydrochloride

By essentially following the procedure in Example 3, substituting 3-bromobenzothiophene for 3-bromofuran, the title compound was prepared with a yield of 82%; mp 216°–218° C. $C_{15}H_{17}NOS \cdot HCl \cdot 0.25H_2O$ requires: C, 60.0; H, 6.2; N, 4.7. Found: C, 60.0; H, 6.2; N, 4.4.

EXAMPLE 12

3-(3-Benzoxazol-2-yl)quinuclidin-3-ol, Oxalate

By essentially following the procedure in Example 1, substituting benzoxazole for thiophene, the title compound was prepared with a yield of 45%; mp 248°–249° C. $C_{14}H_{16}N_2O_2 \cdot 0.5(COOH)_2$ requires: C, 62.3; H, 5.9; N, 9.7. Found: C, 62.4; H, 6.0; N, 9.6.

EXAMPLE 13

3-(Benzothiazol-2-yl)quinuclidin-3-ol, Hydrochloride

By essentially following the procedure in Example 1, substituting benzothiazole for thiophene, the title compound was prepared with a yield of 95%; mp 233°–235° C. $C_{14}H_{16}N_2OS \cdot HCl$ requires: C, 56.6; H, 5.8; N, 9.4. Found: C, 56.6; H, 5.8; N, 9.4.

EXAMPLE 14

3-(2-Thienyl)quinuclidin-2-ene, 0.5 Fumarate 3-(2-Thienyl)quinuclidin-3-ol (2.51 g, 11.98 mmol) prepared in Example 1 was dissolved in concentrated formic acid (15 mL). The solution was refluxed for 2.5 h, alkalinized with 5M sodium hydroxide and extracted with ether. The organic layer was dried over potassium carbonate and concentrated in vacuo to yield 2.10 g (94%) of the product as a yellow oil. The product was converted into the fumarate and recrystallized from MeOH/acetone/Et$_2$O: mp 180°–182° C.; Rf 0.69 in CHCl$_3$/MeOH (95:5) on alumina; $C_{11}H_{13}NS \cdot 0.5C_4H_4O_4$ requires: C, 62.6; H, 6.0; N, 5.6. Found: C, 62.2; H, 6.0; N, 5.6.

EXAMPLE 15

3-(2-Furyl)quinuclidin-2-ene, Oxalate

By essentially following the procedure in Example 14, the title compound was prepared from the 3-(2-furyl)quinuclidin-3-ol prepared in Example 2, with a yield of 91%; mp 144°–144.5° C. $C_{11}H_{13}NO \cdot (COOH)_2$ requires: C, 58.9; H, 5.7; N, 5.3. Found: C, 58.6; H, 5.6; N, 5.1.

EXAMPLE 16

3-[3-Furyl)quinuclidin-2-ene, 0.5 Fumarate

By essentially following the procedure in Example 14, the title compound was prepared from the 3-(3-furyl)quinuclidin-3-ol prepared in Example 3, with a yield of 96%; mp 181.5°–183.5° C. $C_{11}H_{13}NO \cdot 0.5C_4H_4O_4$ requires: C, 66.9; H, 6.5; N, 6.0. Found: C, 66.6; H, 6.6; N, 5.9.

EXAMPLE 17

3-(5-Methyl-2-furyl)quinuclidin-2-ene, 0.5 Fumarate

By essentially following the procedure in Example 14, the title compound was prepared from the 3-(5-methyl-2-furyl)quinuclidin-3-ol prepared in Example 4, with a yield of 93%; mp 159°–160° C. $C_{12}H_{15}NO \cdot 0.5C_4H_4O_4$ requires: C, 68.0; H, 6.9; N, 5.7. Found: C, 67.8; H, 6.9; N, 5.6.

EXAMPLE 18

3-(3-Thienyl)quinuclidin-2-ene, 0.5 Fumarate

By essentially following the procedure in Example 14, the title compound was prepared from the 3-(3-thienyl)quinuclidin-3-ol prepared in Example 5, with a yield of 96%; mp 208°–210° C. $C_{11}H_{13}NS \cdot 0.5C_4H_4O_4$ requires: C, 62.6; H, 6.1; N, 5.6. Found: C, 62.8; H, 6.1; N 5.6.

EXAMPLE 19

3-(5-methyl-2-thienyl)quinuclidin-2-ene, 0.5 Fumarate

By essentially following the procedure in Example 14, the title compound was prepared from the 3-(5-methylthienyl)quinuclidin-3-ol prepared in Example 6, with a yield of 96%; mp 196.5°–198° C. $C_{12}H_{15}NS \cdot 0.5C_4H_4O_4$ requires: C, 63.8; H, 6.5; N, 5.3. Found: C, 63.6; H, 6.5; N, 5.2.

EXAMPLE 20

3-(3-Bromo-2-furyl)quinuclidin-2-ene, Oxalate, 0.75 H$_2$O

By essentially following the procedure in Example 14, the title compound was prepared from the 3-(3-bromo-2-furyl)quinuclidin-3-ol prepared in Example 7, with a yield of 86%; mp 148°–149° C. $C_{11}H_{12}BrNO \cdot (COOH)_2 \cdot 0.75H_2O$ requires: C, 43.6; H, 4.3; N, 3.9. Found: C, 43.6; H, 3.9; N, 3.8.

EXAMPLE 21

3-(5-Ethyl-2-furyl)quinuclidin-2-ene, Fumarate 0.25 H$_2$O

By essentially following the procedure in Example 14, the title compound was prepared from the 3-(5-ethyl-2-furyl)quinuclidin-3-ol prepared in Example 8, with a yield of 96%; mp 81°–83° C. $C_{13}H_{17}NO \cdot C_4H_4O_4 \cdot 0.25H_2O$ requires: C, 63.0; H, 6.7; N, 4.3. Found: C, 63.2; H, 6.5; N, 4.1.

EXAMPLE 22

3-(2-Benzofuryl)quinuclidin-2-ene, 0.5 Fumarate

By essentially following the procedure in Example 14, the title compound was prepared from the 3-(2-benzofuryl)quinuclidin-3-ol prepared in Example 9, with a yield of 92%; mp 216°–217° C. $C_{15}H_{15}NO.0.5C_4H_4O_4$ requires: C, 72.1; H, 6.0; N, 4.9. Found: C, 71.8; H, 6.0; N, 5.0.

EXAMPLE 23

3-(2-Benzothienyl)quinuclidin-2-ene, Hydrochloride

By essentially following the procedure in Example 14, the title compound was prepared from the 3-(2-benzothienyl)quinuclidin-3-ol prepared in Example 10, with a yield of 80%; mp 250°–252° C. $C_{15}H_{15}NS.HCl$ requires: C, 64.9; H, 5.8; N, 5.0. Found: C, 64.8; H, 5.8; N, 5.2.

EXAMPLE 24

3-(3-Benzothienyl)quinuclidin-2-ene, Hydrochloride

By essentially following the procedure in Example 14, the title compound was prepared from the 3-(3-benzothienyl)quinuclidin-3-ol prepared in Example 11, with a yield of 84%; mp 185°–186° C. $C_{15}H_{15}NS.HCl$ requires: C, 64.8; H, 5.8; 5.0. Found: C, 64.8; H, 5.8; N, 5.0.

EXAMPLE 25

3-(Benzothiazol-2-yl)quinuclidin-2-ene Hydrochloride

A mixture of 3-(benzothiazol-2-yl)quinuclidin-3-ol (0.55 g, 2.11 mmol) prepared in Example 13 and methanesulfonic acid (20 mL) was heated neat at 200° C. for 4 hours. Crushed ice (100 g) followed by 5M NaOH (until pH 10 was reached) were carefully added to the reaction mixture. Extraction with ether (4×150 mL), drying ($K_2CO_3$), filtration and concentration in vacuo produced the product as a pale yellow solid. This material was purified by column chromatography on alumina using ether as eluent to yield 0.34 g (66%) of the title compound as a white solid. The base was converted into its hydrochloride and recrystallized from methanol-ether. TLC Rf (free base on alumina)=0.42 (ether); mp 196.5°–198.5° C. $C_{14}H_{14}N_2S.HCl$ requires: C, 60.3; H, 5.4; N, 10.0. Found: C, 60.4; H, 5.5; N, 10.2.

EXAMPLE 26

3-(Benzoxazol-2-yl)-quinuclidin-2-ene, Hydrochloride

By essentially following the procedure described in Example 25, the 3-(benzoxazol-2-yl)quinuclidin-3-ol prepared in Example 12 gave the title compound with a yield of 56%; mp 199.5°–201.5° C. $C_{14}H_{14}N_2O.HCl$ requires: C, 64.0; H, 5.8; N, 10.7. Found: C, 64.0; H, 5.6; N 10.4.

EXAMPLE 27

3-(3-Phenylfuran-2-yl)quinuclidin-2-ene, Oxalate.0.4 $H_2O$

A suspension of 3-(3-bromofuran-2-yl)quinuclidin-2-ene (486.2 mg, 19.1 mmol) in 30 mL of dry dioxane, 67 mg (0.09 mmol) of $PdCl_2(PPh_3)_2$, and 702.5 mg (19.1 mmol) of tributylphenylstannane was refluxed under $N_2$ for 36 hours. During the course of the reaction the colour changed from yellow to black as $Pd^0$ was formed. The reaction mixture was cooled, diluted with ether and filtered through a pad of Celite. Column chromatography on silica using $CHCl_3$/MeOH (85:15) as eluent yielded 250 mg (52%) of the pure compound which was converted into the oxalate and recrystallized from $Et_2O$/MeOH; mp 184°–185° C.; Rf 0.4 in $CHCl_3$/MeOH (85:15). $C_{17}H_{17}NO.(COOH)_2.0.4H_2O$ requires: C, 65.5; H, 5.7; N, 4.0. Found: C, 65.5; H, 5.6; N, 4.0.

EXAMPLE 28

3-(5-Trimethylstannyl-2-furyl)quinuclidin-2-ene 1.5M butyllithium in hexane (18.45 mL, 27.7 mmol) was added dropwise under nitrogen and at room temperature to a solution of 3-(2-furyl)quinuclidin-2-ene (4.15 g, 23.7 mmol) in dry ether (50 mL). After refluxing for 10 min, the mixture was cooled to –70° C., and a solution of $Me_3SnCl$ (4.71 g; 23.68 mmol) in dry ether (20 mL) was added dropwise. After the addition was complete, the mixture was warmed to room temperature and allowed to stir for 2 hours. The reaction mixture was quenched with saturated ammonium chloride (5 mL, added dropwise) and the precipitate (LiCl) was filtered off and discarded. Concentration of the remaining solution followed by column chromatography of the solute on silica using $Et_2O(NH_3)$/MeOH (92:2) as eluent yielded 2.67 g (30%) of the title product. The pure compound was obtained following recrystallization from $Et_2O$/hexane; Rf 0.5 in $Et_2O(NH_3)$/MeOH (9:1) on silica.

EXAMPLE 29

3-(5-Phenylfuran-2-yl)quinuclidin-2-ene, 0.5 Fumarate

A suspension of 3-(5-trimethylstannylfuran-2-yl)quinuclidin-2-ene (46.6 mg, 0.125 mmol), prepared in Example 28, 4.38 mg (0.0062 mmol) of $PdCl_2(PPh_3)_2$, and iodobenzene (25.5 mg, 0.125 mmol) in dry THF (50 mL) was refluxed under $N_2$ for 24 hours. During the course of the reaction the colour changed from yellow to black as $Pd^0$ was formed. The reaction mixture was cooled, diluted with THF and filtered through a pad of Celite. The product was purified on preparative TLC (silica) using $Et_2O(NH_3)$/MeOH (9:1) as eluent to yield 10 mg (32%) of the title compound. The title compound was converted into fumarate and recrystallized from $Et_2O$/MeOH: mp 189°–191° C.; Rf 0.59 in $Et_2O(NH_3)$/MeOH (9:1). Anal. $C_{17}H_{17}NO.0.5C_4H_4O_4.H_2O$ requires: C, 69.7; H, 5.8; N, 4.3. Found: C, 69.8; H, 6.0; N, 4.0.

EXAMPLE 30

3-Tributylstannyl-quinuclidin-2-ene

A solution of 3-quinuclidinone (3.0 g, 24 mmol) in ether (30 mL) was added to a stirred suspension of 2,4,6-triisopropylbenzenesulfonyl hydrazide (7.15 g, 24 mmol) in ether (30 mL). The reaction mixture became homogeneous and was stirred under nitrogen at room temperature over night. The precipitate formed was filtered, and washed with ether to give 7.65 g of 3-(2,4,6-triisopropylbenzenesulfonylhydrazone)quinuclidine (81%) (mp 157°–160° C. $R_f$=0.60 (aluminium oxide, $CHCl_3$+5% MeOH)). A solution of 1.4M n-butyllithium in hexane (13.6 mL, 19.08 mmol) was added dropwise during 15 min. to a stirred slurry of 3-(2,4,6- triisopropylbenzenesulfonylhydrazone)quinuclidine (2.58 g, 6.36 mmol) in TMEDA/hexane (70 mL, 1:1) under nitrogen at −78° C. After stirring for 1 hour at −78° C., the solution was allowed to warm to 0° C. The reaction mixture was cooled on an ice bath until the $N_2$ evolution had ceased (15 min.) and then treated with tributyltin chloride (4.14 g, 12.7 mmol) in TMEDA/hexane (10 mL, 1:1). After stirring for 1.5 hour at 0° C., solid $NH_4Cl$ was added and the mixture was filtrated and concentrated under reduced pressure. The residue was purified by chromatography on aluminium oxide, first with a gradient elution ($CHCl_3 \rightarrow CHCl_3+5\%$ MeOH) and then a second time with ether as eluent to yield 1.85 g of the title compound (4.65 mmol, 73%); $R_f$ (base) 0.61 (aluminium oxide, $CHCl_3+2.5\%$ MeOH).

EXAMPLE 31

3-(2-Methoxycarbonyl-5-furyl)-quinuclidin-2-ene, Oxalate

To a stirred solution of 3-tributylstannylquinuclidin-2-ene (3.43 g, 8.61 mmol), prepared in Example 30, in dioxane (50 mL) were added 2-bromo-5-methoxycarbonylfuran (1.76 g, 8.61 mmol) and $PdCl_2(PPh_3)_2$ (0.18 g, 0.26 mmol). The reaction mixture was refluxed for 5 days under nitrogen. The mixture was concentrated under reduced pressure. The residue was purified by chromatography on aluminium oxide with $CHCl_3$ as eluent and then on $SiO_2$ using $CHCl_3+10\%$ MeOH as eluent and finally on aluminium oxide with ether as eluent. This provided 0.74 g of the title compound (3.19 mmol, 37%) as an oil. The base was converted into the oxalate and recrystallized from MeOH/ether: mp 162°–163° C. Rf (base)=0.42 (aluminium oxide, $CHCl_3$). $C_{13}H_{15}NO_3 \cdot (COOH)_2$ requires: C, 55.7; H, 5.3; N, 4.3. Found: C, 55.6; H, 5.3; N, 4.2.

EXAMPLE 32

3-[5-(N-phenylcarbamoyl)-2-furyl]quinuclidin-2-ene, Oxalate

By essentially following the procedure described in Example 31, substituting 2-(N-phenylcarbamoyl)furan for 2-bromo-5-methoxycarbonylfuran, the title compound was prepared in a yield of 41%; mp 238°–239° C. $C_{18}H_{18}N_2O_2 \cdot (COOH)_2$ requires: C, 62.5; H, 5.2; N, 7.3. Found: C, 62.3; H, 5.3; N, 7.0.

EXAMPLE 33

3-(5-Bromo-2-benzofuryl)quinuclidin-3-ol

3-Ethynyl-3-hydroxyquinuclidine (3.0 g, 19.8 mmol) and 2,6-dibromophenol (5.0 g, 19.8 mmol) were added to a stirred suspension of copper(I)oxide (1.7 g, 11.9 mmol) in dry pyridine (50 mL). The mixture was refluxed under $N_2$ for 15 hours. The solvent was evaporated and the residue was dissolved in $CHCl_3$ and extracted with 1M NaOH. The organic phase was dried ($K_2CO_3$) and concentrated under reduced pressure. The residue was purified by chromatography on aluminium oxide with gradient elution using $CHCl_3 \rightarrow CHCl_3+5\%$ MeOH to yield 1.17 g of product. The solid residue was recrystallized from $CHCl_3$ to yield 0.79 g (12%) of the title compound. Mp 244°–245° C., Rf 0.43 ($Al_2O_3$, $CHCl_3+5\%$ MeOH).

EXAMPLE 34

3-(5-Bromo-2-benzofuryl)quinuclidin-2-ene

By essentially following the procedure in Example 14, the title compound was prepared from the 3-(5-bromo-2-benzofuryl)quinuclidin-3-ol prepared in Example 33.

EXAMPLE 35

3-(5-Butyl-2-furyl)quinuclidin-3-ol

The title compound was prepared by essentially following the procedure in Example 1, substituting 2-butylfuran for thiophene; mp 94°–96° C.

EXAMPLE 36

3-(5-Butyl-2-furyl)quinuclidin-2-ene, Oxalate

The title compound was prepared from the 3-(5-butyl-2-furyl)quinuclidin-3-ol prepared in Example 35 by essentially following the procedure in Example 14; mp 163°–164° C.

EXAMPLE 37

3-(5-Acetyl-2-furyl)quinuclidin-2-ene, Oxalate

The title compound was prepared by following an analogous procedure to the one described in Example 28; mp 166°–167° C.

EXAMPLE 38

3-(4-Acetyl-2-furyl)quinuclidin-2-ene, Oxalate

The title compound was prepared by following an analogous procedure to the one described in Example 27; mp 175°–176° C.

EXAMPLE 39

3-(4-Phenyl-2-furyl)quinuclidin-2-ene, Oxalate

The title compound was prepared by following an analogous procedure to the one described in Example 27; mp 177°–179° C.

EXAMPLE 40

3-(5-Acetyl-2-thienyl)quinuclidin-2-ene, Oxalate

The title compound was prepared by essentially following the procedure in Example 31; mp 184°–185° C.

EXAMPLE 41

3-(5-Formyl-2-thienyl)quinuclidin-2-ene, Oxalate

The title compound was prepared by essentially following the procedure in Example 31; mp 181°–182° C.

EXAMPLE 42

3-(5-Formyl-7-methoxy-2-benzofuryl)quinuclidin-2-ene, Oxalate

The title compound was prepared by essentially following the procedure in Example 33 and Example 14; mp 220° C. (decomp.).

EXAMPLE 43

3-(5-Hydroxymethyl-7-methoxy-2-benzofuryl)quinuclidin-2-ene, Oxalate

The title compound was prepared from 3-(5-formyl-7-methoxy-2-benzofuryl)quinuclidin-2-ene by a reduction using $NaBH_4$ in MeOH; mp 203°–204° C.

EXAMPLE 44

3-(7-Hydroxymethyl-5-iodo-2-benzofuryl)quinuclidin-2-ene, 0.5 Oxalate

The title compound was prepared by following procedures analogous to the ones described in Example 33, Example 14 and Example 43; mp 233°–235° C.

EXAMPLE 45

3-(7-iodo-5-nitro-2-benzofuryl)quinuclidin-2-ene, Oxalate

The title compound was prepared by essentially following the procedures in Example 33 and Example 14; mp 255°–260° C. (decomp.).

EXAMPLE 46

3-(5-cyano-7-iodo-2-benzofuryl)quinuclidin-2-ene, Oxalate

The title compound was prepared by essentially following the procedures in Example 33 and Example 14; mp 255°–265° C. (decomp.).

PREPARATION OF PHARMACEUTICAL COMPOSITIONS

| EXAMPLE A: preparation of tablets | | |
|---|---|---|
| | Ingredients | mg/tablet |
| 1. | Compound in Ex. 27 | 2.0 |
| 2. | Cellulose, microcrystalline | 57.0 |
| 3. | Calcium hydrogen phosphate | 15.0 |
| 4. | Sodium starch glycolate | 5.0 |
| 5. | Silicon dioxide, colloidal | 0.25 |
| 6. | Magnesium stearate | 0.75 |
| | | 80.0 mg |

The title compound in Example 27 is mixed with ingredients 2, 3, 4 and 5 for about 10 minutes. The magnesium stearate is then added, the resultant mixture being mixed for about 5 minutes and then compressed into tablet form with or without film-coating.

| EXAMPLE B: preparation of capsules | | |
|---|---|---|
| | Ingredients | mg/capsule |
| 1. | Compound in Ex. 21 | 2 |
| 2. | Lactose | 186 |
| 3. | Corn Starch | 20 |
| 4. | Talc | 15 |
| 5. | Magnesium stearate | 2 |
| | | 225 mg |

The title compound in Example 21 is mixed with ingredients 2 and 3 and then milled. The resulting mixture is mixed with ingredients 4 and 5 and then filled into capsules of appropriate size.

BIOLOGICAL EVALUATION

The biological activity of compounds of the present invention was tested using several tests.

Receptor Binding Assay

The affinity of the compounds was determined for muscarinic receptor subtypes in the cerebral cortex, parotid gland, heart and bladder preparations from guinea pig by their ability to displace radiolabeled quinuclidinyl benzilate, a well-known muscarinic receptor antagonist. The experimental conditions are described in detail by L. Nilvebrant and B. Sparf in Eur. J. Pharmacol. 1986, 123, 133. The results are presented in Table 1 below.

Functional In Vitro Studies

Male guinea pigs, weighing about 300 g, were killed by a blow on the neck and exsanguinated. Smooth muscle strips of the urinary bladder and ileum (longitudinal muscle only) were dissected in a Krebs-Henseleit solution (pH 7.4). The strip preparations were then vertically mounted between two hooks in thermostatically controlled (37° C.) organ baths (5 mL). One of the hooks was adjustable and connected to a force transducer (FT 03, Grass Instruments). The Krebs-Henseleit solution was continuously bubbled with carbogen gas (93.5% $O_2$/6.5% $CO_2$) to maintain pH at 7.4. Isometric tension was recorded by a Grass Polygraph (model 79D). A resting tension of approximately 5 mN was initially applied on each muscle strip and the preparations were allowed to stabilize for at least 45 min. The resting tension was repeatedly adjusted and the preparations were washed several times during the stabilization period.

The urinary bladder strips were used for evaluation of antimuscarinic activity and the ileal preparations for studies of muscarinic activity. Carbachol (carbamylcholine chloride) was used as the standard agonist. Concentration-response curves to agonists were generated either by the cumulative dose-response technique (bladder strip) or by the addition of single agonist concentrations (ileal preparations). In the latter case, the preparations were washed and allowed to rest between each concentration of agonist. $EC_{50}$ values were graphically determined.

In studies of antagonism, a control concentration-response curve to carbachol was generated by cumulative addition of carbachol to the bladder strip (i.e., stepwise increase of the agonist concentration until the maximal contractile response was reached), followed by washing out and a resting period of at least 15 min. before a fix concentration of the test compound (antagonist) was added to the organ-bath. After 60 min. of incubation, a second cumulative concentration-response curve to carbachol was generated. Responses were expressed as percent of the maximal response to carbachol. $EC_{50}$-values for carbachol in the absence (control) and presence of antagonist were graphically derived and dose ratios (r) were calculated. Dissociation constants, $K_b$, for the antagonists were then calculated using the following equation (1), where [A] is the concentration of test compound.

$$K_b=[A]/r-1 \qquad (1)$$

The results of the above described functional in vitro studies are presented in Table 1 below together with the results from the receptor binding assay described further above; the data for the agonistic effect on ileum is in relation to maximal carbachol response ($E_{max}$).

TABLE 1

| Compound Ex. | Cortex (nM) | Heart (nM) | Parotis (nM) | Bladder (nM) | $K_b$ | Ileum |
|---|---|---|---|---|---|---|
| 1 | 12000 | >23000 | 49000 | 45000 | 40000 | |
| 3 | | | | | 87000 | |
| 4 | | | | | 1200 | |
| 5 | | | | | 84000 | |
| 6 | | | | | 23000 | |
| 7 | 4900 | 10000 | 20000 | 12000 | 11000 | |
| 8 | | | | | 6700 | |
| 9 | | | | | 720 | |
| 10 | | | | | 3700 | |
| 11 | | | | | 4300 | |
| 12 | | | | | 3900 | |
| 13 | 1200 | 3000 | 3800 | 8100 | 4200 | |
| 14 | | | | | 1100 | |
| 15 | | | | | 550 | |
| 16 | | | | | 3400 | |
| 17 | | | | | 61 | |
| 18 | 710 | 1700 | 2600 | 3700 | 2000 | |
| 19 | | | | | 320 | 10% at 500 µM |
| 21 | | | | | 31 | |
| 22 | | | | | 33 | |
| 23 | | | | | 660 | |
| 24 | | | | | 170 | |
| 25 | | | | | 810 | |
| 26 | 170 | 600 | 1100 | 760 | 190 | |
| 27 | | | | | 2.7 | |
| 29 | | | | | 1020 | |
| 31 | | | | | 2600 | 21% at 500 µM |

From Table 1 above, the substantial increase in antagonism obtained by introducing the double bond into the quiniclidine ring is readily seen when comparing the data for the quinuclidinol compounds 1 to 13 with the data for the corresponding quinuclidinenes 14 to 26.

We claim:

1. A compound of the general Formula I:

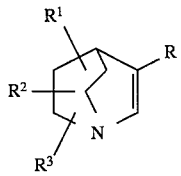

wherein

R is a group of the general Formula II or III:

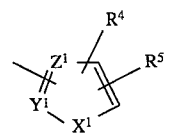

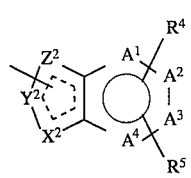

where $X^1$ represents oxygen or sulphur and $Y^1$ and $Z^1$ both represent carbon;

one of $X^2$, $Y^2$ and $Z^2$ represents oxygen or sulphur and the other two both represent carbon or one represents nitrogen and the other represents carbon, and the dotted line in Formula III represents an optional additional carbon-carbon or carbon-nitrogen bond;

$A^1$, $A^2$, $A^3$ and $A^4$ each represent carbon or, when one of $X^2$, $Y^2$ and $Z^2$ represents oxygen or sulphur and the other two both represent carbon, one of $A^1$, $A^2$, $A^3$ and $A^4$ may represent nitrogen and the others carbon;

$R^1$, $R^2$ and $R^3$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $C_{1-10}$alkoxy, $C_{2-10}$alkenyloxy, $C_{2-10}$alkynyloxy, $C_{3-10}$cycloalkyloxy, $C_{5-10}$cycloalkenyloxy, $C_{4-10}$cycloalkylalkoxy, $C_{6-10}$cycloalkylalkenyloxy, hydroxy, hydroxy-$C_{1-10}$alkyl, or $(CH_2)_nAr$, where Ar is an optionally substituted aryl selected from the group consisting of phenyl and naphthyl or heteroaryl, the latter containing 1 to 3 heteroatoms selected from oxygen, sulphur and nitrogen and being selected from the group consisting of thiophene, furan, pyrrole, imidazole, pyrazole, thiazole, isothiazole, oxazole, isoxazole, triazole, pyridine, benzofuran, isobenzofuran, benzothiazole, benzothiophene, indole, isoindole, oxadiazole and benzooxazole and n is an integer 0 to 10; and $R^4$ and $R^5$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, halogen or $(CH_m)_nB$, wherein $(CH_m)_n$, in which n is as defined above and m independently is an integer 0 to 2, represents a bond or a straight or branched, saturated or unsaturated hydrocarbon chain and B represents Ar (as defined above), $COR^6$, $COOR^6$, $CON(R^6)_2$, $N(R^6)_2$, $OR^6$, CN, $NO_2$, C=$NOR^6$, $OCOR^6$, $N(R^6)COR^6$, $C(R^6)_2OR^6$, $OCOC(OH)(R^6)_2$ or trifluoromethyl where $R^6$ independently represents hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $(CH_2)_nAr$ or a bi- or tricyclic ring system, wherein Ar and n are as defined above; or $R^4$ and $R^5$ are interconnected to complete a saturated or unsaturated ring which may contain 1 or 2 hetero atoms;

with the proviso that when R represents a group of Formula II and $R^1$, $R^2$ and $R^3$ each are hydrogen, R is other than 2-furyl, 4-methyl-2-furyl and 5-methyl-2-furyl; and physiologically acceptable salts thereof.

2. A compound according to claim 1, wherein $R^1$, $R^2$ and $R^3$ each represent hydrogen.

3. A compound according to claim 1 or 2, wherein R is a group of Formula II where $X^1$ represents oxygen or sulphur and $Y^1$ and $Z^1$ are carbon, or a group of Formula III where $A^1$ to $A^4$ each represent carbon and one of $X^2$, $Y^2$ and $Z^2$ represents oxygen or sulphur and the others represent carbon.

4. A compound according to claim 3, wherein R is a group of Formula II and $X^1$ represents oxygen, or R is a group of Formula III and said one of $X^2$, $Y^2$ and $Z^2$ represents oxygen.

5. A compound according to claim 4, wherein $R^4$ and $R^5$ are selected from hydrogen, $C_{1-10}$alkyl, optionally substituted aryl or heteroaryl and $(CH_m)_nB$, where $(CH_m)_n$ is methylene, ethylene, allylene, vinylene or acetylene and B is $N(R^6)_2$, $OR^6$, C=NOH, $OCOR^6$, $N(R^6)COR^6$ or $C(R^6)_2OR^6$ where $R^6$ independently is hydrogen, $C_{1-6}$alkyl, $C_{2-6}$alkenyl, $C_{2-6}$alkynyl, $C_{3-8}$cycloalkyl, $C_{3-8}$cycloalkenyl or optionally substituted phenyl or furyl.

6. A compound according to claim 5, wherein one of $R^4$ and $R^5$ represents hydrogen and the other represents $C_{1-10}$alkyl or optionally substituted aryl selected from the group consisting of phenyl and naphthyl, preferably $C_{1-6}$alkyl or optionally substituted phenyl.

7. A compound according to claim 1 selected from:
3-(2-furyl)quinuclidin-2-ene;
3-(3-furyl)quinuclidin-2-ene;
3-(5-ethyl-2-furyl)quinuclidin-2-ene;
3-(3-bromo-2-furyl)quinuclidin-2-ene;
3-(3-thienyl)quinuclidin-2-ene;
3-(2-thienyl)quinuclidin-2-ene;
3-(5-methyl-2-furyl)quinuclidin-2-ene;
3-(3-phenyl-2-furyl)quinuclidin-2-ene;
3-(5-methyl-2-thienyl)quinuclidin-2-ene;
3-(5-phenyl-2-furyl)quinuclidin-2-ene;
3-(3-methyl-2-furyl)quinuclidin-2-ene;
3-(5-methoxycarbonyl-2-furyl)-quinuclidin-2-ene;
3-(2-benzofuryl)quinuclidin-2-ene;
3-(5-bromo-2-benzofuryl)-quinuclidin-2-ene;
3-(2-benzothienyl)quinuclidin-2-ene;
3-(3-benzothienyl)quinuclidin-2-ene;
3-(benzothiazol-2-yl)quinuclidin-2-ene;
3-[5-(N-phenylcarbamoyl)-2-furyl]-quinuclidin-2-ene;
3-(benzoxazol-2-yl)quinuclidin-2-ene;
3-(5-butyl-2-furyl)quinuclidin-2-ene;
3-(5-acetyl-2-furyl)quinuclidin-2-ene;
3-(4-acetyl-2-furyl)quinuclidin-2-ene;
3-(4-phenyl-2-furyl)quinuclidin-2-ene;
3-(5-acetyl-2-thienyl)quinuclidin-2-ene;
3-(5-formyl-2-thienyl)quinuclidin-2-ene;
3-(5-formyl-7-methoxy-2-benzofuryl)quinuclidin-2-ene;
3-(5-hydroxymethyl-7-methoxy-2-benzofuryl)quinuclidin-2ene;
3-(7-hydroxymethyl-5-iodo-2-benzofuryl)quinuclidin-2-ene;
3-(7-iodo-5-nitro-2-benzofuryl)quinuclidin-2-ene;
3-(5-cyano-7-iodo-2-benzofuryl)quinuclidin-2-ene;
and physiologically acceptable salts thereof.

8. A pharmaceutical composition comprising a compound of the general Formula I:

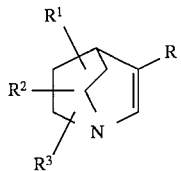

wherein

R is a group of the general Formula II or III:

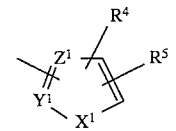

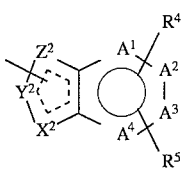

where $X^1$ represents oxygen or sulphur and $Y^1$ and $Z^1$ both represent carbon;

one of $X^2$, $Y^2$ and $Z^2$ represents oxygen or sulphur and the other two both represent carbon or one represents nitrogen and the other represents carbon, and the dotted line in Formula III represents an optional additional carbon-carbon or carbon-nitrogen bond;

$A^1$, $A^2$, $A^3$ and $A^4$ each represent carbon or, when one of $X^2$, $Y^2$ and $Z^2$ represents oxygen or sulphur and the other two both represent carbon, one of $A^1$, $A^2$, $A^3$ and $A^4$ may represent nitrogen and the others carbon;

$R^1$, $R^2$ and $R^3$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $C_{1-10}$alkoxy, $C_{2-10}$alkenyloxy, $C_{2-10}$alkynyloxy, $C_{3-10}$cycloalkyloxy, $C_{5-10}$cycloalkenyloxy, $C_{4-10}$cycloalkylalkoxy, $C_{6-10}$cycloalkylalkenyloxy, hydroxy, hydroxy-$C_{1-10}$alkyl, or $(CH_2)_n Ar$, where Ar is an optionally substituted aryl selected from the group consisting of phenyl and naphthyl or heteroaryl, the latter containing 1 to 3 heteroatoms selected from oxygen, sulphur and nitrogen and being selected from the group consisting of thiophene, furan, pyrrole, imidazole, pyrazole, thiazole, isothiazole, oxazole, isoxazole, triazole, pyridine, benzofuran, isobenzofuran, benzothiazole, benzothiophene, indole, isoindole, oxadiazole and benzooxazole and n is an integer 0 to 10; and $R^4$ and $R^5$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, halogen or $(CH_m)_n B$, wherein $(CH_m)_n$, in which n is as defined above and m independently is an integer 0 to 2, represents a bond or a straight or branched, saturated or unsaturated hydrocarbon chain and B represents Ar (as defined above), $COR^6$, $COOR^6$, $CON(R^6)_2$, $N(R^6)_2$, $OR^6$, $CN$, $NO_2$, $C=NOR^6$, $OCOR^6$, $N(R^6)COR^6$, $C(R^6)_2 OR^6$, $OCOC(OH)(R^6)_2$ or trifluoromethyl, where $R^6$ independently represents hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $(CH_2)_n Ar$ or a bi- or tricyclic ring system, wherein Ar and n are as defined above; or $R^4$ and $R^5$ are interconnected to complete a saturated or unsaturated ring which may contain 1 or 2 hetero atoms; in association with a pharmaceutically acceptable carrier.

9. A process for the preparation of a compound of the general Formula I as defined in claim 1, which process comprises:

(a) dehydrating a compound of the general Formula IV:

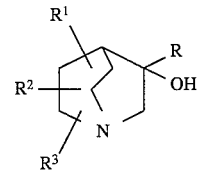

wherein R, $R^1$, $R^2$ and $R^3$ are as defined in claim 1; or (b) for the preparation of a compound of Formula I wherein $R^4$ and $R^5$ are as defined in claim 1 except that $R^5$ is other than hydrogen, reacting, in the presence of a metal catalyst, a compound of the general Formula V or VI:

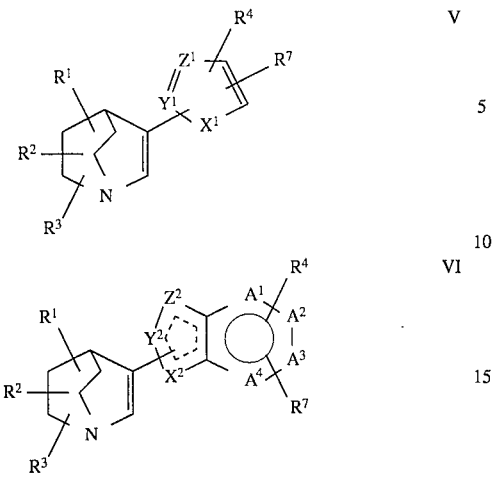

with a compound $R^8$-D, wherein $X^1, Y^1, Z^1, X^2, Y^2, Z^2$ and $R^4$ are as defined in claim 1, D is $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $(CH_2)_nAr$ or $(CH_m)_nB$, where Ar, n, m and B are as defined in claim 1, and one of $R^7$ and $R^8$ represents halogen, triflate or mesylate and the other represents a group selected from $Sn(Alk)_3$, $Si(Alk)_3$, ZnHal, $Al(R^9)_2$, $TlX_2$, HgX, and $B(OR^9)_2$, where Alk is alkyl of from 1 to 10 carbon atoms, Hal is halogen, X is halogen, acetate or trifluoroacetate, and $R^9$ is hydrogen or Alk, or $R^7$ represents halogen, triflate or mesylate and $R^8$-D is $C_{2-10}$alk-1-yn;

c) for the preparation of a compound of Formula I wherein $R^4$ and $R^5$ are as defined in claim 1 except that $R^5$ is other than hydrogen, generating the carbanion of a compound of the general Formula VII or VIII:

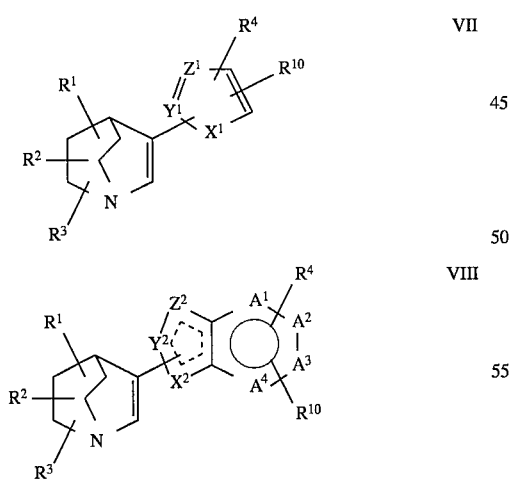

wherein $X^1, Y^1, Z^1, X^2, Y^2, Z^2$ and $R^4$ are as defined in claim 1, and $R^{10}$ represents hydrogen or halogen, and reacting the carbanion formed with an electrophilic reagent capable of forming the desired substitutent $R^5$;

(d) reacting, in the presence of a metal catalyst, a compound of the general Formula IX:

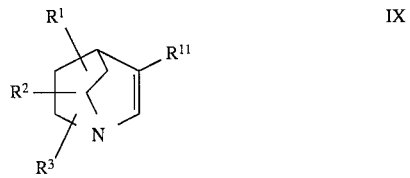

with a compound R—E, wherein R, $R^1$, $R^2$ and $R^3$ are as defined in claim 1, and one of $R^{11}$ and E represents halogen, triflate or mesylate and the other represents a group selected from $Sn(Alk)_3$, $Si(Alk)_3$, ZnHal, $Al(R^9)_2$, $TlX_2$, HgX and $B(OR^9)_2$, where Alk is alkyl of from 1 to 10 carbon atoms, Hal is halogen, X is halogen, acetate or trifluoroacetate, and $R^9$ is hydrogen or Alk, (e) for the preparation of compounds of Formula I, wherein R is a group Formula III, in which $A^1$ to $A^4$ each are carbon or one of $A^1$ to $A^4$ are nitrogen and the others are carbon, $X^2$ is oxygen or sulphur and $Y^2$ and $Z^2$ both are carbon, reacting a compound or intermediate of the general Formula X:

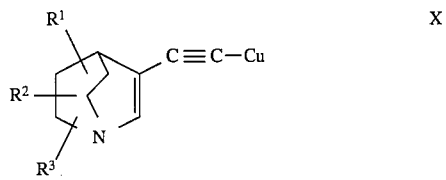

wherein $R^1$, $R^2$ and $R^3$ are as defined in claim 1, with a compound of the general Formula XI:

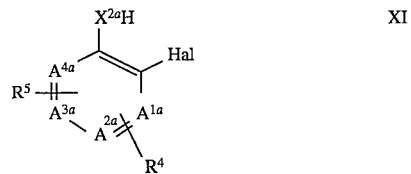

wherein $R^4$ and $R^5$ are as defined in claim 1, Hal represents halogen, $X^{2a}$ represents oxygen or sulphur, and $A^{1a}$ to $A^{4a}$ each represent carbon or one of $A^{1a}$ to $A^{4a}$ represent nitrogen and the others represent carbon;

(f) for the preparation of compounds of Formula I, wherein R is a group Formula III, in which $A^1$ to $A^4$ each are carbon or one of $A^1$ to $A^4$ are nitrogen and the others are carbon, $X^2$ is oxygen or sulphur and $Y^2$ and $Z^2$ both are carbon, reacting a compound or intermediate of the general Formula XII:

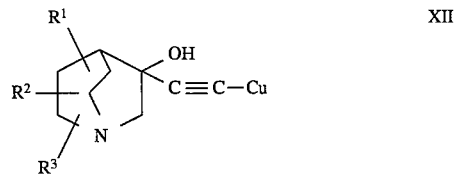

wherein $R^1$, $R^2$ and $R^3$ are as defined in claim 1, with a compound of Formula XI as defined in process e) above, and then dehydrating the product formed;

(g) in a compound of Formula I, converting a group $R^4$ or $R^5$ into another group $R^4$ or $R^5$;

and, if desired, forming a physiologically acceptable salt with an organic or inorganic acid.

10. A compound of the general Formula IV:

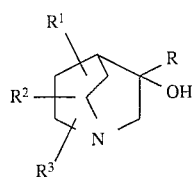

wherein

R is a group of the general Formula II or III:

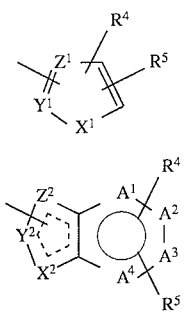

where $X^1$ represents oxygen or sulphur and $Y^1$ and $Z^1$ both represent carbon;

one of $X^2$, $Y^2$ and $Z^2$ represents oxygen or sulphur and the other two both represent carbon or one represents nitrogen and the other represents carbon, and the dotted line in Formula III represents an optional additional carbon-carbon or carbon-nitrogen bond;

$A^1$, $A^2$, $A^3$ and $A^4$ each represent carbon or, when one of $X^2$, $Y^2$ and $Z^2$ represents oxygen or sulphur and the other two both represent carbon, one of $A^1$, $A^2$, $A^3$ and $A^4$ may represent nitrogen and the others carbon;

$R^1$, $R^2$ and $R^3$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $C_{1-10}$alkoxy, $C_{2-10}$alkenyloxy, $C_{2-10}$alkynyloxy, $C_{3-10}$cycloalkyloxy, $C_{5-10}$cycloalkenyloxy, $C_{4-10}$cycloalkylalkoxy, $C_{6-10}$cycloalkylalkenyloxy, hydroxy, hydroxy-$C_{1-10}$alkyl, or $(CH_2)_nAr$, where Ar is an optionally substituted aryl selected from the group consisting of phenyl and naphthyl or heteroaryl, the latter containing 1 to 3 heteroatoms selected from oxygen, sulphur and nitrogen and being selected from the group consisting of thiophene, furan, pyrrole, imidazole, pyrazole, thiazole, isothiazole, oxazole, isoxazole, triazole, pyridine, benzofuran, isobenzofuran, benzothiazole, benzothiophene, indole, isoindole, oxadiazole and benzooxazole and n is an integer 0 to 10; and $R^4$ and $R^5$ independently represent hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, halogen or $(CH_m)_nB$, wherein $(CH_m)_n$, in which n is as defined above and m independently is an integer 0 to 2, represents a bond or a straight or branched, saturated or unsaturated hydrocarbon chain and B represents Ar (as defined above), $COR^6$, $COOR^6$, $CON(R^6)_2$, $N(R^6)_2$, $OR^6$, CN, $NO_2$, $C=NOR^6$, $OCOR^6$, $N(R^6)COR^6$, $C(R^6)_2OR^6$, $OCOC(OH)(R^6)_2$ or trifluoromethyl, where $R^6$ independently represents hydrogen, $C_{1-10}$alkyl, $C_{2-10}$alkenyl, $C_{2-10}$alkynyl, $C_{3-10}$cycloalkyl, $C_{5-10}$cycloalkenyl, $C_{4-10}$cycloalkylalkyl, $C_{6-10}$cycloalkylalkenyl, $(CH_2)_nAr$ or a bi- or tricyclic ring system, wherein Ar and n are as defined above; or $R^4$ and $R^5$ are interconnected to complete a saturated or unsaturated ring which may contain 1 or 2 heteroatoms;

with the proviso that when R represents a group of Formula II and $R^1$, $R^2$ and $R^3$ each are hydrogen, R is other than 2-furyl, 4-methyl-2-furyl and 5-methyl-2-furyl;

and salts thereof.

11. A method for the treatment and/or prophylaxis of a disease or disorder, wherein said disease or disorder is selected from the group consisting of dementia, spastic states of the gastrointestinal tract, peptic ulcers, incontinence and bradycardia, comprising:

administering to a patient, in need thereof, an effective amount of a compound, as defined in claim 1.

* * * * *